United States Patent [19]

McGrath

[11] Patent Number: 5,690,958
[45] Date of Patent: Nov. 25, 1997

[54] UNIT DOSE CHLORHEXADINE GLUCONATE(CHG) APPLICATOR HAVING EXTENDED CHG SHELF LIFE

[75] Inventor: Patrick D. McGrath, Lenexa, Kans.

[73] Assignee: Medi-Flex Hospital Products, Inc., Overland Park, Kans.

[21] Appl. No.: 723,686

[22] Filed: Sep. 30, 1996

[51] Int. Cl.⁶ ..................................................... A61K 9/48
[52] U.S. Cl. .......................... 424/451; 424/405; 424/409; 424/412; 514/945
[58] Field of Search .................... 424/443, 448, 424/449, 405, 409, 412, 451; 604/3; 514/945; 128/759, 760, 762, 761, 771

[56] References Cited

U.S. PATENT DOCUMENTS

| | | | |
|---|---|---|---|
| 2,253,287 | 8/1941 | Davis et al. | 128/335.5 |
| 2,361,413 | 10/1944 | Pujol Y Font | 226/20 |
| 3,531,300 | 9/1970 | Greenberg et al. | 99/214 |
| 3,598,517 | 8/1971 | Beecher | 21/58 |
| 3,619,126 | 11/1971 | Carvallo | 21/56 |
| 3,725,003 | 4/1973 | Moore et al. | 21/58 |
| 3,754,368 | 8/1973 | Moore et al. | 53/21 |
| 3,986,832 | 10/1976 | Smorenburg | 21/80 |
| 4,088,444 | 5/1978 | Byrne | 21/56 |
| 4,832,965 | 5/1989 | Helin | 426/66 |
| 4,981,678 | 1/1991 | Tomlinson | 424/45 |
| 4,989,733 | 2/1991 | Patry | 206/570 |
| 5,103,836 | 4/1992 | Goldstein et al. | 128/760 |
| 5,538,353 | 7/1996 | DeHavilland | 401/132 |

Primary Examiner—Thurman K. Page
Assistant Examiner—Kathryne E. Shelborne
Attorney, Agent, or Firm—Shook, Hardy & Bacon L.L.P.

[57] ABSTRACT

A unit dose chlorhexadine gluconate (CHG) applicator is disclosed wherein a unit dose of the CHG is contained in a hermetically sealed manually crushable glass ampule that has an internal volume not significantly greater than the unit dose volume of the CHG. The CHG in the ampule has an effective shelf life of at least 24 months. The glass ampule of the applicator is preferably protected by a flexible cover to protect the user's hand during manual crushing of the ampule to release the CHG therefrom. In one embodiment of the invention, a cylindrical glass ampule is housed within a tubular, flexible synthetic resin cover which has a porous applicator swab at one end thereof. Upon crushing of the glass ampule, the CHG released therefrom impregnates the swab allowing the user to spread the CHG across an area to be sanitized. In a second embodiment of the invention, a cylindrical glass ampule is received within a semi-cylindrical, open-sided body cover having a flange portion that mounts a sponge-like swab communicating with the interior of the body cover. Opposed integral wing-like gripping members on the ampule permit the user to crush the ampule by squeezing the members toward one another whereupon the CHG is released from the ampule and impregnates the sponge swab. The swab soaked with the CHG antiseptic may be rubbed across an area to be sanitized.

14 Claims, 1 Drawing Sheet

U.S. Patent  Nov. 25, 1997  5,690,958
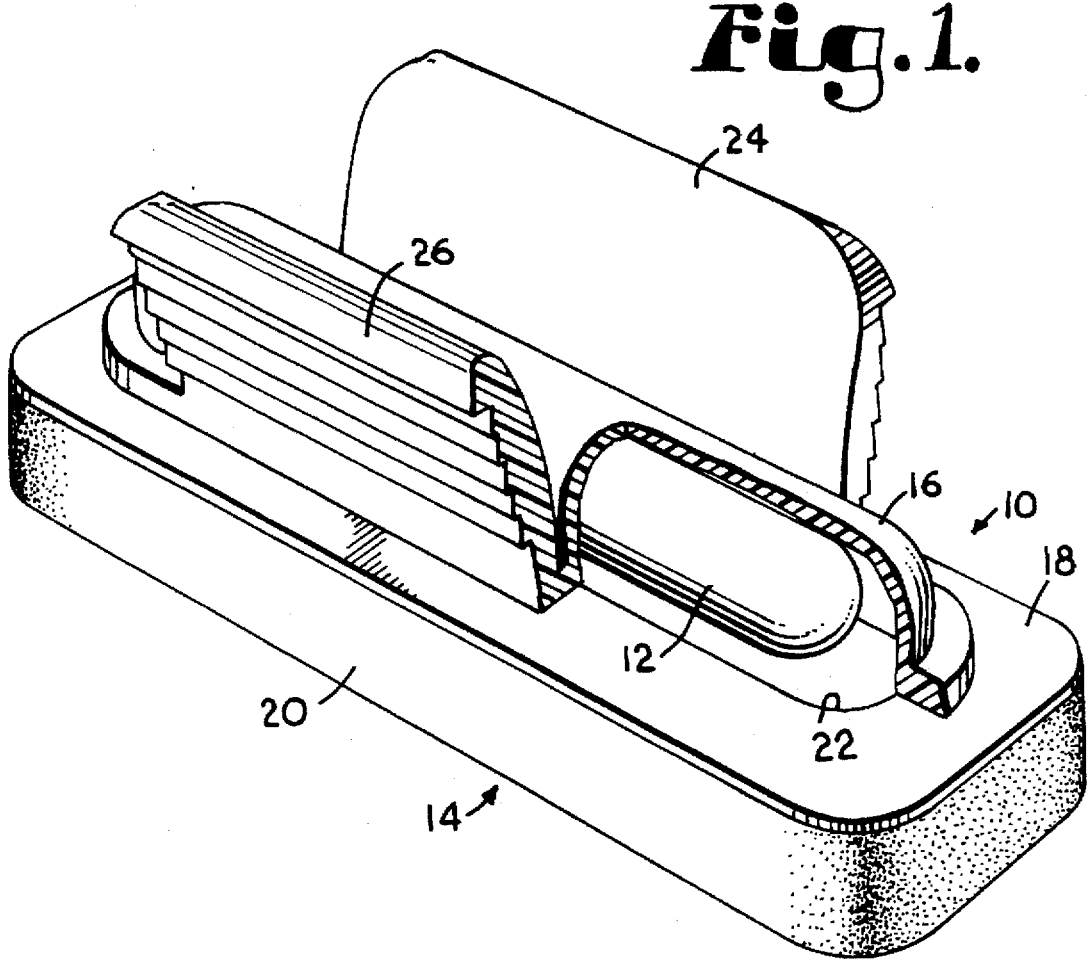
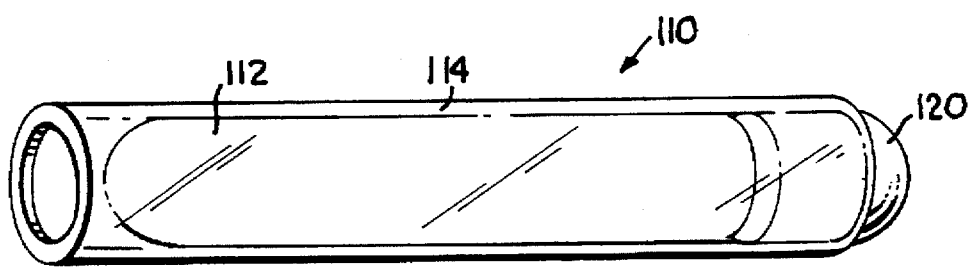

UNIT DOSE CHLORHEXADINE GLUCONATE(CHG) APPLICATOR HAVING EXTENDED CHG SHELF LIFE

BACKGROUND OF THE INVENTION

1. Field of the Invention

This invention relates to an improved antiseptic composition and particularly to chlorhexadine gluconate (CHG) antiseptic which is packaged as a unit dose in a manner to facilitate application of the antiseptic while at the same time exhibiting a longer shelf life than previously attainable with conventional fabric prep pad CHG dispensers.

2. Description of the Prior Art

CHG has long been used as an antiseptic composition for sterilizing selected areas of a patient's skin prior to injection of medicinal agents, or preparatory to other medical or surgical procedures. Application of the antiseptic solution to the patient's skin has been facilitated by packaging in a variety of configurations including bulk dose volumes in plastic bottles and single dose volumes in a multi-layer foil unit encasing a fabric prep pad soaked with what amounts to a unit dose of the active solution.

In order to commercialize any package of CHG or other medicament, it is required that stability in the selected container closure be demonstrated for the duration of the proposed shelf-life. In view of the fact that a desired shelf-life of two to three years is desirable, the stability study duration prior to marketing can be substantial. Heat accelerated studies are commonly employed to reduce the time required to establish two-year or three-year shelf lives. In heat accelerated studies, packages of medication are exposed to elevated temperatures, often around 40° C., for three to six months. Demonstration of drug recoveries which are still within specification at the completion of these studies allows projection of stability at room temperature for periods beyond that actually measured under room temperature conditions. By employing heat accelerated studies it is thereby possible to defend a proposed shelf-life of two years with studies of actual duration substantially less than two years.

It has been known for some time that CHG is subject to chemical instability under elevated temperature conditions. Government regulatory agencies have expressed reservations about accepting accelerated shelf-life tests of packages of CHG in support of extended shelf-life projections. This Government resistance is believed to have been founded primarily on the belief that CHG will undergo significant deterioration at elevated temperatures. Thus, the accelerated test with significant molecular degradation was felt to be not predictive of stability and therefore not useful for projecting stability at ambient conditions beyond the period of actual ambient measurement. Manufacturers of unit dose CHG packages faced requirements to establish projected shelf-life without the assistance of heat accelerated studies.

Instability of CHG under elevated temperature conditions also presented a problem with regard to sterilization of the package by conventional elevated temperature ethylene oxide (ETO) sterilization techniques. During ETO sterilization CHG containers are typically placed in an enclosed space and the temperature is raised to level from about 120° F. to about 140° F. in the presence of an atmosphere of ETO. Thereafter, a vacuum is imposed on the space to remove ETO from the interior of the packages while the temperature of the space is allowed to subside to ambient. This entire package sterilization procedure usually requires two to three days. This degree of heat exposure can result in significant degradation of CHG in typical fabric pad unit dose configurations.

It has been known for some time that rayon-containing fabric resulted in reductions of recoverable CHG, with such reductions demonstrating apparent saturability, as might be consistent with physical adsorbtion. Efforts were made to produce stable unit dose packages of CHG using fabric materials for pads which were rayon-free; however, these efforts were not completely successful. Even with the use of rayon-free pad materials, instability upon exposure to heat was significant. The mechanism for CHG instability to heat has not been fully defined though it may be attributable to an unavoidable property of a molecular structure with a variety of opportunities for rotational or vibrational motion and/or ring opening. On the basis of all prior knowledge it is reasonable to conclude that instability under conditions of elevated temperature is an inherent property of the CHG molecule not amenable to control by packaging techniques.

SUMMARY OF THE INVENTION

During empirical studies relating to the effects of temperature on CHG products, it has now been unexpectedly discovered that the CHG stability under conditions of elevated temperature can be extended over that of typical unit dose package configurations by a packaging configuration which involves the retention of the CHG solution within a hermetically sealed glass ampule with no contact between the solution and the fabric applicator until the time of use.

It is therefore a primary object of the present invention to provide a unit dose CHG applicator which exhibits a significantly greater CHG shelf life than previously available unit dose CHG packages, even after ETO sterilization of the applicator under a relatively high temperature.

This invention involves the discovery that by confining a unit dose of CHG in an elongated, manually-crushable glass unit dose ampule or vial which has been hermetically sealed using flame closure of the filling end of the glass ampule, the antiseptic composition has a significantly longer shelf life than heretofore attainable with multi-layer foil prep pad packages for the CHG.

In particular, this invention involves the surprising discovery that when a unit dose of CHG is packaged in a glass ampule having an internal volume not significantly greater than the volume of the unit dose, the glass ampule containing a unit dose of CHG can be subjected to a meaningful accelerated, elevated temperature shelf-life test without significant adverse affect on the CHG within the glass ampule.

It is a further important object of the invention to provide a unit dose CHG applicator having an extended CHG shelf life which lends itself to ease of application of the antiseptic solution by virtue of the fact that the user may simply crush the glass ampule containing the CHG to release the antiseptic into an integral porous pad, and then rub that pad across the portion of the patient's skin to be sterilized.

A protective cover is provided over the glass ampule containing the CHG solution to protect the user's hand from glass shards created during crushing of the unit dose glass container. In one embodiment of the applicator, the ampule is of cylindrical shape and the protective cover thereover is also of cylindrical configuration and has a porous swab or tip at one end which becomes soaked with the antiseptic solution upon fracture of the liquid-filled vial. The user may then apply the antiseptic agent to a patient's skin by simply rubbing the soaked swab tip across the area to be sterilized.

In a second embodiment of the invention, a cylindrical ampule containing the CHG antiseptic composition is housed within a protective cover assembly having a central body section enclosing the ampule, and two wing-like gripping members on opposite sides of the cover body and thereby the ampule. The cover body has an elongated opening communicating the interior thereof with a sponge-like member that is an integral part of the assembly. Thus, upon manual manipulation of the wing-like members toward one another, the cover body is compressed thereby fracturing the glass ampule and releasing the CHG composition to effect impregnation of the sponge member with the antiseptic solution. The antiseptic-soaked sponge member may then be rubbed across that part of the patient's skin to be sterilized.

It is theorized that the unit dose CHG applicator of this invention has improved shelf life over previously available CHG dispensers by virtue of the fact that the active ingredient in unit dose form is introduced into and maintained within a substantially inert environment that does not change significantly during package sterilization or extended storage periods under varying ambient temperature conditions. The favorable storage conditions are obtained by incorporating a unit dose of the CHG in a hermetically sealed glass vial ampule which has an internal volume not significantly greater than the volume of the antiseptic dose. The initially open end of the glass ampule is subjected to an open flame to melt the glass and cause it to coalesce into a closure. The flame also serves to increase the temperature of the atmosphere immediately above the unit dose of CHG in the ampule, so that upon closing of the ampule, the volume of the ampule above the unit dose has a very limited oxygen content because of expansion of the air above the unit dose at the time of hermetic sealing of the glass ampule. In certain instances, the rarefied atmosphere above the unit dose in the ampule may be at a negative pressure upon cooling of the ampule as a result of the heating of such atmosphere which took place during the ampule sealing process. As a consequence, the CHG remains fully isolated throughout storage from conditions or material such as a fabric prep pad that would otherwise be conducive to degradation or deterioration of the active material. Furthermore, the glass ampule has a much smaller surface area per total volume of CHG, i.e., total contact area per total volume of active agent, than was the case with the fabric prep pads encased in a foil cover. In addition, the glass has a more oxygen-starved atmosphere than was the case with the fabric pads. The ability to increase the temperature of the atmosphere overlying the CHG during sealing of the container using the open flame as described, thus decreasing the amount of oxygen present in the final atmosphere overlying the unit dose of antiseptic solution in the glass ampule, as compared with packaging methods available for preparation of fabric pads packaged in foil covers, also is believed to have an affect on avoidance of degradation of the CHG during storage of the unit doses of the antiseptic.

Notwithstanding full protection of the CHG from reduction in recoverable active ingredient, ease of application is retained in that the user is required only to manually crush the glass vial and apply the antiseptic which has soaked the scrub pad or tip directly to the area to be sanitized. Tests have demonstrated that CHG packaged as set out herein has a predicted shelf life of at least two years, and under most ambient conditions should be even longer than two years.

BRIEF DESCRIPTION OF THE DRAWINGS

FIG. 1 is a perspective view of a unit dose CHG applicator constructed in accordance with one preferred embodiment of the invention, with parts being broken away and in section for clarity; and FIG. 2 is a perspective view of a unit dose CHG applicator constructed in accordance with a second preferred embodiment of the invention.

DETAILED DESCRIPTION OF THE PREFERRED EMBODIMENTS

Referring initially to FIG. 1 of the drawings, a unit dose CHG applicator is broadly designated by the numeral 10 and in its preferred embodiment includes a frangible glass vial or ampule 12 of generally cylindrical configuration. Ampule 12 is closed at both ends with the initially open, fill end having been hermetically sealed by application of an open flame to the fill end to melt and cause the glass at such fill end to coalesce and form an air-tight closure. The internal volume of ampule 12 is not significantly greater than the volume of CHG that is introduced into and stored in sealed glass vial 12.

Applicator 10 includes a cover body assembly broadly designated 14 for ampule 12 that is constructed and configured so that it may for example be fabricated by molding of the assembly from a synthetic resin material such as high density polyethylene. The semi-cylindrical wall structure 16 of assembly 14 is flexible and of a size and shape to complementally receive and substantially house the elongated cylindrical ampule 12. Flange panel 18 joined to and integral with the peripheral edge of wall structure 16 projects outwardly therefrom and serves to mount a rectangular porous sponge element 20. It is to be perceived from FIG. 1 that flange panel 18 has an elongated opening 22 therein communicating the interior of wall structure 16 with sponge 20.

A pair of opposed, generally upright, angularly-inclined gripping members 24 and 26 also integral with wall structure 16 along the major lengths of the elongated opening 22, are of wing-like configuration and are juxtaposed in disposition such that when the gripping members 24 and 26 are grasped between the fingers of a user and squeezed toward one another, wall structure 16 is compressed thereby exerting compressive forces on the side wall of vial 12 and effecting fracturing of the vial 12.

When the ampule 12 is crushed, the CHG solution contained therein is released so that it may flow through opening 22 and soak the sponge 20 with the active ingredient. The user may then swab the patient's skin area to be sanitized while grasping the wing-like members 24 and 26 to manipulate applicator 10.

Applicator 10 is preferably packaged in a protective envelope for sanitary purposes which may be made up of a paper layer on one side of the applicator and a thin film transparent sheet of plastic on the other side thereof. The overall package is then subjected to ETO sterilization as previously described.

It is to be understood in this respect that applicator 10 may, if desired, be constructed and used in accordance with the applicator structure shown and described in U.S. Pat. No. 5,538,353 entitled Liquid Applicator and which issued Jul. 23, 1996 to the assignee hereof and that is incorporated herein by specific reference thereto.

Alternatively, a unit dose CHG applicator 110 may be constructed in accordance with the showing of FIG. 2 of the drawings hereof. In the FIG. 2 embodiment of the present invention, elongated cylindrical glass vial or ampule 112 is complementally housed within an elongated cylindrical, flexible, synthetic resin cover 114 of a size to fully encase the vial 112. A porous applicator swab 120 is fitted within one end of applicator cover 114, extends outwardly therefrom and desirably rests against an adjacent extremity of ampule 112. The applicator 110 is also preferably packaged in an envelope having a paper layer and a thin film plastic layer which are laminated together and subjected to elevated temperature ETO sterilization.

A user desiring to sanitize a selected skin area of a patient may simply crush vial 112 by applying adequate forces to the protective cover 114 to break the side wall of the glass vial. The antiseptic solution released from the broken vial is quickly absorbed by the porous tip 120 thus permitting the user to apply antiseptic solution directly to the area of the patient's skin to be sanitized.

In the preparation of unit dose applicators 10 and 110, it first is necessary to provide a thin wall glass ampule having a normally open end. The glass ampule is preferably of cylindrical configuration and of a wall thickness permitting it to be readily crushed and broken between the user's fingers. The internal volume of the glass ampule should not be significantly greater than the volume of the antiseptic to be stored therein.

After filling of each vial, the normally open end is sealed to present a hermetically-sealed container. An open flame is preferably used to effect sealing of the initially open end of the glass ampule. The flame is applied to the glass vial for a time sufficient to melt the glass and cause the melt to coalesce and effect an air-tight closure of the vial. The flame used to effect hermetic sealing of the glass ampule serves the secondary purpose of increasing the temperature of the gaseous atmosphere overlying the unit dose of CHG within the glass ampule so that upon closure of such ampule and subsequent cooling of the atmosphere above the unit dose of CHG, the gaseous atmosphere within the ampule above the CHG agent is at a pressure somewhat lower than the pressure that existed within the glass vial prior to hermetic sealing. In view of the decrease in the density of the gaseous atmosphere overlying the CHG antiseptic agent within the ampule, there is less oxygen available to react with the CHG over time, than would be the case if air at atmospheric pressure was retained within the ampule over the CHG at the time of sealing of the ampule.

Upon cooling of the hermetically-sealed glass body containing the antiseptic agent, the filled glass ampule may be placed within a respective cover assembly 14 or 114 whereupon the product is ready for packaging and distribution.

A unit dose of CHG generally is about 1 ml and nominally contains about 2 wt. %/vol of CHG. If the wt. %/vol of the CHG falls to a level of about 1.8% or less during storage over a 24 month period, the product is not deemed to have an acceptable storage life. Thus, in certain instances, suppliers of CHG in unit dosage form have in the past provided an excess of the CHG solution over that specifically required to provide an initial 1 ml volume of active agent, in order to compensate for lost of active material during storage.

It has now been discovered, contrary to the recognized procedures of prior test protocols, that the shelf life of a dose unit of CHG stored in an applicator therefor may be determined by subjecting the filled glass ampule to an elevated temperature for a period significantly less than the actual demonstrable shelf life of the product. For example, where it is desired that a product have a shelf life of at least about 24 months, the shelf life at normal ambient conditions can be predicted by subjecting an applicator containing a dose unit of CHG to an elevated temperature of about 40° C. for no more than about six months, and usually no more than three months. Accelerated heating testing of fabric prep pads is not equally predictive of shelf life because under the elevated temperature conditions of the test, the CHG undergoes undesirable degradation and deteriorization that has no relationship to storage conditions and effects.

EXAMPLE 1

The shelf life of multi-layer foil packages each containing a prep pad and a dose unit of CHG was tested using the 40° C. elevated temperature test environment described above, and also tested at an ambient temperature of about 72° F. In order to provide a more accurate determination of the extent of degradation or deterioration, if any, of CHG stored in foil packets each having a non-rayon prep pad therein, samples were prepared having 1.0 ml, 1.1 ml and 1.2 ml of CHG per unit dose prep pad package. Furthermore, the CHG was assayed for recoverable CHG prior to introduction into respective foil packages followed by sealing of the edges of the packages. The foil packets containing active ingredient and prep pads were enclosed in a protective paper and plastic film envelope and then subjected to ETO sterilization at a temperature of from about 120° F. to about 140° F. in accordance with the standard procedure previously described.

The stability tests demonstrated that the dosage forms exhibited a significant reduction in CHG recovery as soon as one month after initiation of the test. Not unexpectedly, the dosage forms filled with greater volumes of CHG provided greater CHG recoveries. The foil packages each containing a prep pad and that were maintained at ambient temperatures had a slower continued loss of CHG than the foil packages with prep pads subjected to the accelerated 40° C. stability test environment. However, in all instances the tests showed that the shelf life of the CHG was adversely affected by the presence of the prep pads even though such prep pads were of the non-rayon type.

Chlorhexidine Gluconate Stability in Fabric (prep pad) Applicators % w/v CHG[1]

| | Heat Accelerated (40° C.) | | | | Ambient | | |
|---|---|---|---|---|---|---|---|
| Age Days | 1.0 ml Fill | 1.1 ml Fill | 1.2 ml Fill | Age Days | 1.0 ml Fill | 1.1 ml Fill | 1.2 ml Fill |
| 0 | 2.17 | 2.17 | 2.17 | 0 | 2.17 | 2.17 | 2.17 |
| 7 | 2.02 | 2.08 | 2.12 | 20 | 2.02 | 2.08 | 2.12 |
| 40 | 1.86 | 1.87 | 1.91 | 40 | 2.03 | 1.98 | 1.99 |
| 49 | 1.87 | 1.84 | 1.88 | | | | |
| 58 | 1.81 | 1.84 | 1.85 | 62 | 1.99 | 2.05 | 2.03 |
| 69 | 1.81 | 1.83 | 1.89 | 82 | 1.97 | 1.99 | 1.96 |
| 125 | 1.76 | 1.80 | 1.80 | 138 | 1.95 | 2.01 | 1.97 |

[1]Between day 0 and day 20 ambient conditions, samples were subject to heat of ETO sterilization.

EXAMPLE II

The shelf life of CHG in a glass ampule such as the ampules depicted by the numerals 12 and 112 in FIGS. 1 and 2 of the drawings hereof were also tested using the 40° C. elevated temperature test environment described above, and also tested at an ambient temperature of about 72° F. These test samples were subjected to an ETO sterilization temperature between days 0 and 20 in the same manner as was carried out in connection with the tests described in Example I hereof. The results of these accelerated tests were as follows:

|  | Heat (40° C.) | | | | | | Ambient | | | | | |
|  | 507014 | | 507015 | | 507016 | | 507014 | | 507015 | | 507016 | |
|  | Sepp[1] | Frepp[2] | Sepp | Frepp | Sepp | Frepp | Sepp | Frepp | Sepp | Frepp | Sepp | Frepp |
| --- | --- | --- | --- | --- | --- | --- | --- | --- | --- | --- | --- | --- |
| Bulk | 2.0 | 2.0 | 1.9 | 1.9 | 2.1 | 2.1 | 2.0 | 2.0 | 1.9 | 1.9 | 2.1 | 2.1 |
| Time 0 | 2.1 | 2.1 | 2.1 | 2.1 | nodata | 2.1 | 2.1 | 2.0 | 2.1 | 2.1 | 2.1 | 2.1 |
| Month 2–3 | nodata | nodata | 1.9 | 1.9 | nodata | nodata | nodata | 2.0 | 2.0 | 2.0 | 2.1 | 2.0 |
| Month 4–6 | 1.9 | | 1.9 | 1.9 | | 2.0 | 2.0 | 2.1 | 2.1 | 2.1 | 2.1 | 2.1 |

[1]Sepp - Ampule of FIG. 2 of the drawings herein.
[2]Frepp - Ampule of FIG. 1 of the drawings herein

I claim:

1. A bactericidal agent dosage applicator having an extended shelf life comprising:

a unit dose of chlorhexadine gluconate; and a manually crushable glass ampule containing said unit dose of chlorhexadine gluconate, the internal volume of said ampule not being significantly greater than the volume of said unit dose, said glass ampule having an extremity which was closed at the time of filling of the ampule with the chlorhexadine gluconate and an extremity which was heat-sealed after filling of the ampule with the chlorhexadine gluconate to provide a hermetic closure for the ampule.

2. A bactericidal agent dosage applicator as set forth in claim 1 wherein said heat-sealed extremity of the ampule was subjected to a flame sufficient to melt the glass and provide the hermetic closure.

3. A bactericidal agent dosage applicator as set forth in claim 1 wherein said glass ampule is of generally cylindrical shape and said extremities are at opposite ends thereof.

4. A bactericidal agent dosage applicator as set forth in claim 1 wherein said glass ampule containing the chlorhexadine gluconate unit dose was subjected to elevated temperature sterilization after introduction of the chlorhexadine gluconate into the interior thereof and hermetic sealing of the ampule.

5. A bactericidal agent dosage applicator as set forth in claim 1 wherein is provided a flexible cover over said glass ampule to protect the user's hand during manual crushing of the ampule to release the chlorhexadine gluconate therefrom.

6. A bactericidal agent dosage applicator as set forth in claim 5 wherein is provided means associated with said flexible cover for causing the chlorhexadine gluconate to be directionally released from the ampule upon manual crushing of the latter.

7. A bactericidal agent dosage applicator as set forth in claim 5 wherein said cover has an opening therein communicating with the exterior surface of the ampule, and a porous applicator swab carried by the cover and extending through said opening.

8. A bactericidal agent dosage applicator as set forth in claim 5 wherein said ampule is elongated and the cover has an opening therein extending along the longitudinal length of the ampule, and applicator sponge means on the cover extending along the length of the opening therein in disposition to receive chlorhexadine gluconate released from the ampule upon crushing thereof.

9. A method of preparing a bactericidal agent dosage applicator having an extended shelf life comprising:

providing a manually crushable glass ampule having a closed extremity and an initially open extremity;

introducing a unit dose of chlorhexadine gluconate into the ampule, said ampule having an internal volume not significantly greater than the unit dose volume of the chlorhexadine gluconate; and subjecting the initially open extremity of the ampule to heat at a temperature and for a time sufficient to melt the glass defining said initially open extremity and form a closure therefor upon cooling of the heated glass to effect hermetic sealing of the chlorhexadine gluconate within the ampule.

10. A method of preparing a bactericidal agent dosage applicator as set forth in claim 9 wherein is included the step of subjecting the glass ampule containing the chlorhexadine gluconate unit dose to elevated temperature sterilization prior to heat sealing of the ampule.

11. A method of preparing a bactericidal agent dosage applicator as set forth in claim 10 wherein said sterilization step includes subjecting the glass ampule containing the chlorhexadine gluconate unit dose to a temperature of from about 120° F. to about 140° F.

12. A method of preparing a bactericidal agent dosage applicator as set forth in claim 9 wherein heat sealing of said initially open extremity of the ampule is effected by subjecting such extremity to an open flame.

13. A method of preparing a bactericidal agent dosage applicator as set forth in claim 9 wherein is included the step of placing a flexible cover over the hermetically sealed glass ampule to protect the user's hand during manual crushing of the ampule to release the chlorhexadine gluconate therefrom.

14. A method of preparing a dosage unit of chlorhexadine gluconate and of conducting an accelerated test to verify that such dosage unit has an extended shelf life of at least about twenty-four months comprising the steps of:

providing a manually crushable glass ampule having a closed extremity and an initially open extremity;

introducing a unit dose of chlorhexadine gluconate into the ampule, said ampule having an internal volume not significantly greater than the unit dose volume of the chlorhexadine gluconate;

subjecting the initially open extremity of the ampule to heat at a temperature and for a time sufficient to melt the glass defining said initially open extremity and form a closure therefor upon cooling of the heated glass to effect hermetic sealing of the chlorhexadine gluconate within the ampule;

placing the hermetically sealed ampule in a elevated temperature environment of about 40° C. for approximately three months; and thereafter breaking the ampule, recovering a sample of the chlorhexadine gluconate contained therein and testing such sample to determine the extent of degradation if any of the chlorhexadine gluconate unit dose.

\* \* \* \* \*